(12) United States Patent
Kaiami

(10) Patent No.: US 10,856,762 B2
(45) Date of Patent: Dec. 8, 2020

(54) ATRIAL FIBRILLATION DETECTOR, ATRIAL FIBRILLATION DETECTING METHOD, AND COMPUTER READABLE MEDIUM

(71) Applicant: NIHON KOHDEN CORPORATION, Tokyo (JP)

(72) Inventor: Takashi Kaiami, Tokorozawa (JP)

(73) Assignee: NIHON KOHDEN CORPORATION, Tokyo (JP)

(*) Notice: Subject to any disclaimer, the term of this patent is extended or adjusted under 35 U.S.C. 154(b) by 274 days.

(21) Appl. No.: 15/851,892

(22) Filed: Dec. 22, 2017

(65) Prior Publication Data

US 2018/0177420 A1   Jun. 28, 2018

(30) Foreign Application Priority Data

Dec. 26, 2016   (JP) ................................. 2016-251031

(51) Int. Cl.
 *A61B 5/046* (2006.01)
 *A61B 5/00* (2006.01)
 (Continued)

(52) U.S. Cl.
 CPC ............ *A61B 5/046* (2013.01); *A61B 5/0006* (2013.01); *A61B 5/02116* (2013.01);
 (Continued)

(58) Field of Classification Search
 CPC ... A61B 5/046; A61B 5/02116; A61B 5/0006; A61B 5/04012; A61B 5/02405; A61B 5/02125
 See application file for complete search history.

(56) References Cited

U.S. PATENT DOCUMENTS 6,081,745 A * 6/2000 Mehra .................. A61N 1/3956
                                                      607/4
2006/0052704 A1   3/2006 Baba et al.
(Continued)

FOREIGN PATENT DOCUMENTS

JP   S57-195438 A   12/1982
JP   2000-000218 A   1/2000
(Continued)

OTHER PUBLICATIONS

Japanese Office action issued in Japanese Patent Application No. 2016-251031 dated Sep. 8, 2020.

*Primary Examiner* — Mark Bockelman
(74) *Attorney, Agent, or Firm* — Pearne & Gordon LLP

(57) ABSTRACT

An atrial fibrillation detecting device includes a processor and a memory that stores a computer-readable command. When the computer-readable command is executed by the processor, the atrial fibrillation detecting device is configured to acquire pulse data representing a plurality of pulses, calculate a pulse rate based on the pulse data, calculate respective pulse amplitude indices of the plurality of pluses based on the pulse data, calculate an amplitude dispersion of the pulse amplitude indices based on the calculated pulse amplitude indices, calculate respective pulse interval indices of the plurality of pluses based on the pulse data, calculate an interval dispersion of the pulse interval indices based on the calculated pulse interval indices, and determine whether the pulse data is atrial fibrillation, based on the calculated pulse rate, the calculated amplitude dispersion, and the calculated interval dispersion.

14 Claims, 6 Drawing Sheets

(51) Int. Cl.
  *A61B 5/021* (2006.01)
  *A61B 5/024* (2006.01)
  *A61B 5/04* (2006.01)

(52) U.S. Cl.
  CPC ....... *A61B 5/02125* (2013.01); *A61B 5/02405* (2013.01); *A61B 5/04012* (2013.01)

(56) References Cited

U.S. PATENT DOCUMENTS

| | | |
|---|---|---|
| 2006/0241359 A1 | 10/2006 | Nagai et al. |
| 2007/0123787 A1 | 5/2007 | Kitajima et al. |
| 2010/0081947 A1 | 4/2010 | Suzuki |
| 2012/0095358 A1 | 4/2012 | Matsunaga et al. |
| 2016/0051154 A1 | 2/2016 | Iwawaki |
| 2016/0135717 A1 | 5/2016 | Koivisto et al. |

FOREIGN PATENT DOCUMENTS

| | | |
|---|---|---|
| JP | 2006-102489 A | 4/2006 |
| JP | 2006-296940 A | 11/2006 |
| JP | 2007-125366 A | 5/2007 |
| JP | 2012-081194 A | 4/2012 |
| JP | 5336803 B2 | 11/2013 |
| JP | 2016-043041 A | 4/2016 |
| JP | 2016-526409 A | 9/2016 |

\* cited by examiner

_US 10,856,762 B2_

ATRIAL FIBRILLATION DETECTOR, ATRIAL FIBRILLATION DETECTING METHOD, AND COMPUTER READABLE MEDIUM

CROSS REFERENCE TO RELATED APPLICATION

This application is based on Japanese Patent Applications No. 2016-251031 filed on Dec. 26, 2016, the contents of which are incorporated herein by reference.

BACKGROUND

The present disclosure relates to an atrial fibrillation detecting device and an atrial fibrillation detecting method. In addition, the present disclosure relates to a computer-readable storage medium in which a program for making a computer execute the atrial fibrillation detecting method is stored.

Japanese Patent No. 5336803 discloses a pulse measuring device which calculates each pulse amplitude and each pulse interval respectively, calculates a product of the pulse amplitude and the pulse interval and a ratio between the pulse amplitude and the pulse interval, and determines that the pulses indicate an arrhythmia, based on the product of the pulse amplitude and the pulse interval and the ratio between the pulse amplitude and the pulse interval.

However, the pulse measuring device disclosed in Japanese Patent No. 5336803 can determine whether the pulses indicate an arrhythmia or not, but cannot determine whether the pulses indicate premature ventricular contraction or indicate atrial fibrillation.

The present disclosure is to provide an atrial fibrillation detecting device and an atrial fibrillation detecting method which detects atrial fibrillation more accurately.

Further, the present disclosure is to provide a computer-readable storage medium in which a program for making a computer execute the atrial fibrillation detecting method is stored.

SUMMARY

According to an aspect of the present disclosure, an atrial fibrillation detecting device includes a processor and a memory that stores a computer-readable command. When the computer-readable command is executed by the processor, the atrial fibrillation detecting device acquires pulse data representing a plurality of pulses, calculates a pulse rate based on the pulse data, calculates respective pulse amplitude indices of the plurality of pluses based on the pulse data, calculates an amplitude dispersion of the pulse amplitude indices based on the calculated pulse amplitude indices, calculates respective pulse interval indices of the plurality of pluses based on the pulse data, calculates an interval dispersion of the pulse interval indices based on the calculated pulse interval indices, and determines whether the pulse data is atrial fibrillation, based on the calculated pulse rate, the calculated amplitude dispersion, and the calculated interval dispersion.

According to another aspect of the present disclosure, an atrial fibrillation detecting method that is executed by a computer includes acquiring pulse data representing a plurality of pulses, calculating a pulse rate based on the pulse data, calculating respective pulse amplitude indices of the plurality of pluses based on the pulse data, calculating an amplitude dispersion of the pulse amplitude indices based on the calculated pulse amplitude indices, calculating respective pulse interval indices of the plurality of pluses based on the pulse data, calculating an interval dispersion of the pulse interval indices based on the calculated pulse interval indices, and determining whether the pulse data is atrial fibrillation, based on the calculated pulse rate, the calculated amplitude dispersion, and the calculated interval dispersion.

According to the present disclosure, it is possible to provide an atrial fibrillation detecting device and an atrial fibrillation detecting method which detects atrial fibrillation more accurately. Further, according to the present disclosure, it is possible to provide a computer-readable storage medium in which a program for making a computer execute the atrial fibrillation detecting method is stored.

DETAILED DESCRIPTION OF EMBODIMENTS

A presently disclosed subject matter will be described below with reference to the drawings. Incidentally, description about elements having one and the same reference signs as elements which have already been described in description of the presently disclosed subject matter will be omitted for convenience of explanation.

Figure 1:
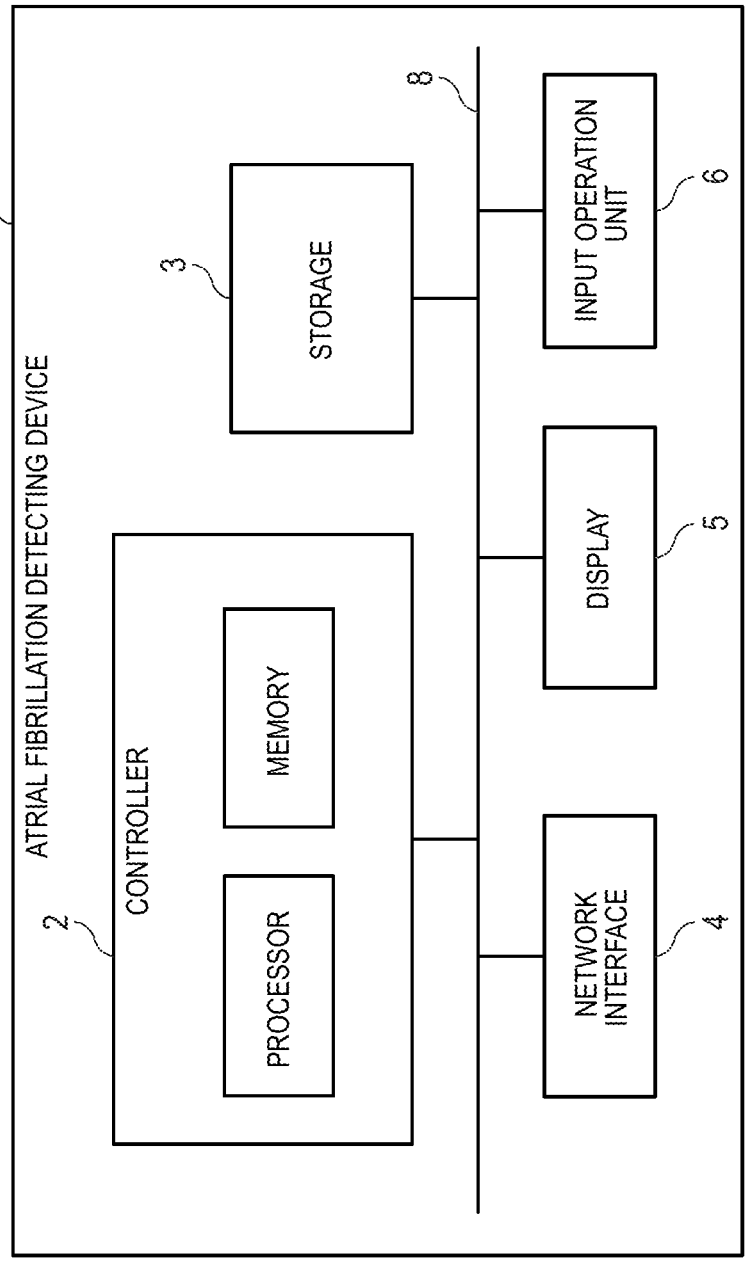
FIG. 1 is a hardware configuration diagram illustrating an atrial fibrillation detecting device according to a presently disclosed subject matter.

FIG. 1 illustrates a hardware configuration diagram of an atrial fibrillation detecting device 1 according to the presently disclosed subject matter. As illustrated in FIG. 1, the atrial fibrillation detecting device 1 (which will be hereinafter referred to as detecting device 1 simply) may include a controller 2, a storage 3, a network interface 4, a display 5, and an input operation unit 6, which are connected to one another communicably through a bus 8.

The detecting device 1 may be a medical dedicated device (such as a patient monitor) for displaying a trend graph or a list of vital data. For example, a personal computer, a work station, a smartphone, a phablet, a tablet, or a wearable device (such as an Apple Watch or a smart glass) which is mounted on a body part (such as an arm or the head) of an operator (medical care provider) may be used as the detecting device 1.

The controller 2 may include a memory and a processor. The memory is configured to store computer-readable commands (programs). For example, the memory is constituted by an ROM (Read Only Memory) in which various programs etc. have been stored, an RAM (Random Access Memory) which has a plurality of work areas where the various programs etc. to be executed by the processor can be stored, etc. For example, the processor may be a CPU (Central Processing Unit), an MPU (Micro Processing Unit) and/or a GPU (Graphics Processing Unit), which is configured to expand a program onto the RAM to execute various processes in cooperation with the RAM. The program is specified from the various programs which have been incorporated in the ROM.

The controller 2 may control various operations of the detecting device 1 in such a manner that, particularly, the processor expands an atrial fibrillation detecting program for executing an undermentioned atrial fibrillation detecting method onto the RAM, and executes the atrial fibrillation detecting program in cooperation with the RAM. The controller 2 and the atrial fibrillation detecting program will be described later in detail.

Figure 4:
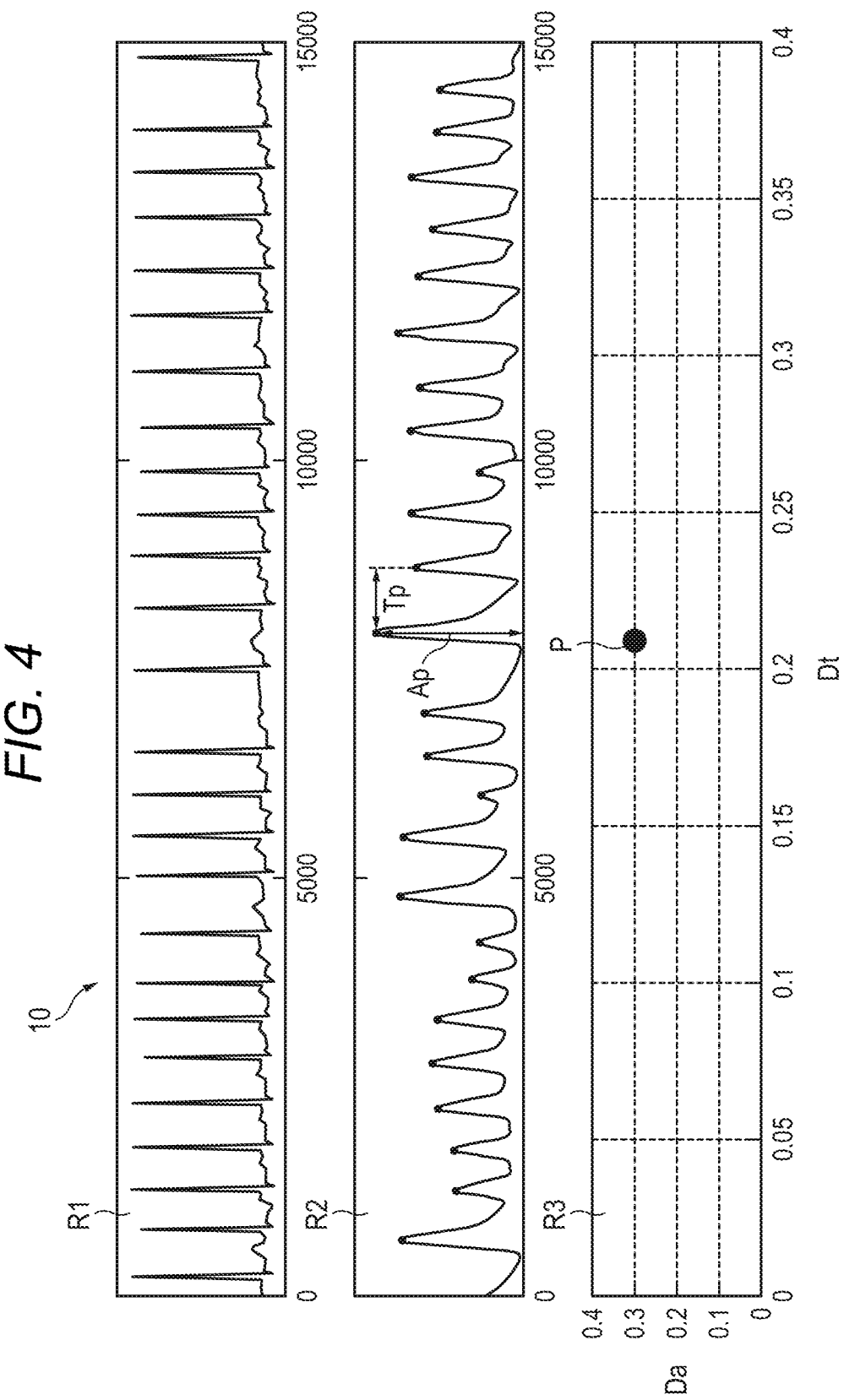
FIG. 4 illustrates an example of a physiological information display screen which can include the pulse analysis result display region displayed as a two-dimensional coordinate system.

For example, the storage 3 is a storage device (storage) such as an HDD (Hard Disk Drive), an SSD (Solid State Drive) or a USB flash memory, which is configured to store the programs or various data. The atrial fibrillation detecting program may be incorporated in the storage 3. In addition, ECG data representing an ECG waveform or pulse data representing pulses may be stored in the storage 3. The ECG data are acquired by a not-illustrated ECG sensor. Further, the pulse data are acquired by a not-illustrated pulse sensor. The acquired ECG data or the acquired pulse data may be stored into the storage 3 through a communication network or through a storage medium such as a USB memory, or may be stored into the storage 3 through a sensor interface (not illustrated) connected to the ECG sensor or the pulse sensor. As shown in FIG. 4, the ECG waveform is constituted by heartbeat waveforms occurring continuously along a time axis (see an ECG waveform display region R1). In addition, the pulses occur continuously along the time axis (see a pulse display region R2).

The network interface 4 is configured to connect the detecting device 1 to the communication network. Specifically, the network interface 4 may include various wired connection terminals for making communication with an external device such as a server through the communication network, and various processing circuits for wireless connection. The network interface 4 is configured to be conformed to communication standards for making communication through the communication network. Here, the communication network may be an LAN (Local Area Network), a WAN (Wide Area Network), the Internet, or the like. For example, the atrial fibrillation detecting program or the vital data (the ECG data or the pulse data) may be acquired through the network interface 4 from a computer disposed on the communication network.

Figure 5:
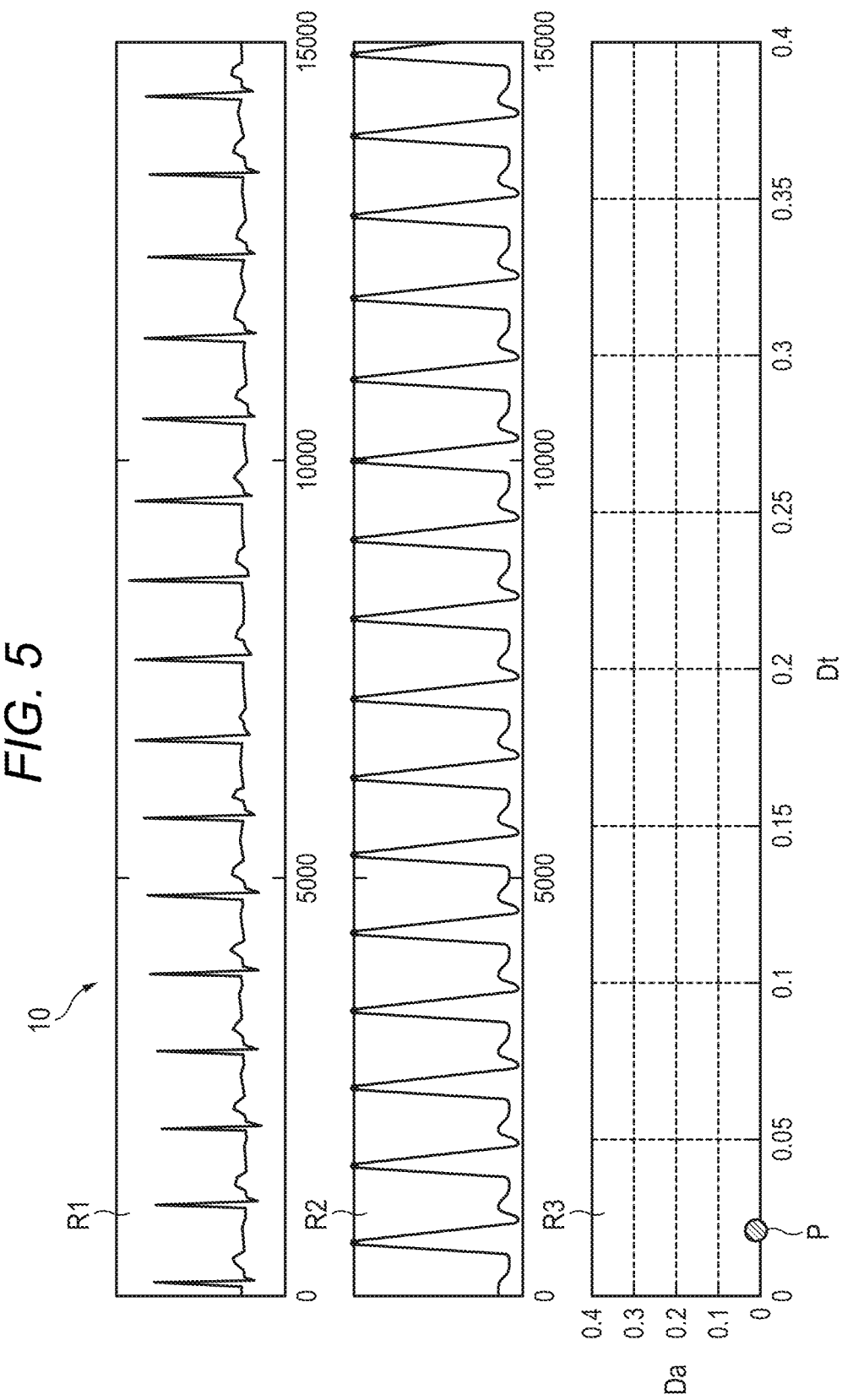
FIG. 5 illustrates another example of the physiological information display screen which can include the pulse analysis result display region displayed as the two-dimensional coordinate system.
Figure 6:
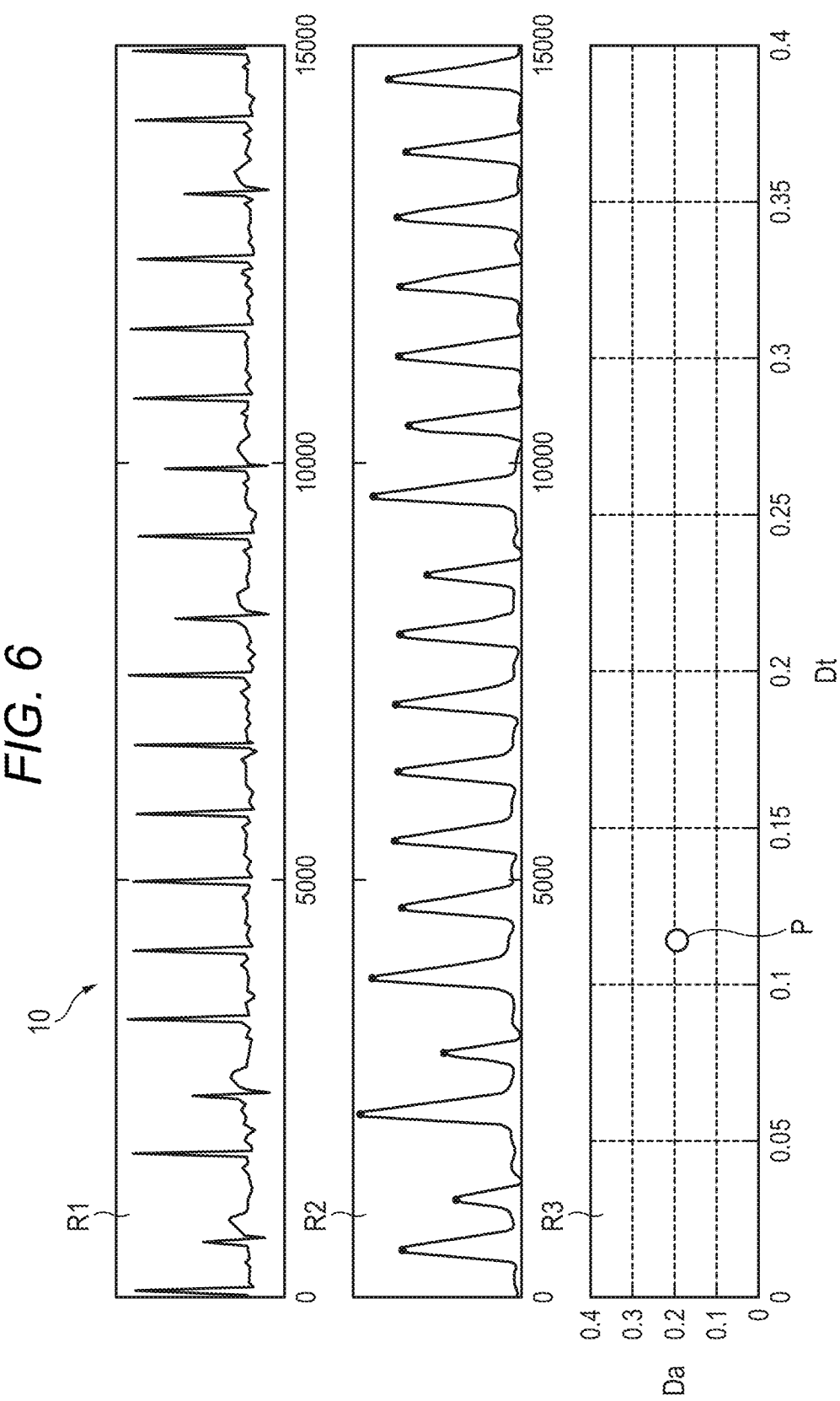
FIG. 6 illustrates a further example of the physiological information display screen which can include the pulse analysis result display region displayed as the two-dimensional coordinate system.

The display 5 may be a display device such as a liquid crystal display, an organic EL display, or a transmissive type or non-transmissive type head mount display which is to be mounted on the head of the operator. For example, as illustrated in FIGS. 4 to 6, a physiological information display screen 10 is displayed on a display screen of the display 5.

The input operation unit 6 accepts an input operation from the operator operating the detecting device 1, and is configured to generate an instruction signal in response to the input operation. For example, the input operation unit 6 is a touch panel superimposed and disposed on the display 5, operation buttons attached to a housing, a mouse or a keyboard, or the like. The instruction signal generated by the input operation unit 6 is transmitted to the controller 2 through the bus 8. The controller 2 executes predetermined processing in accordance with the instruction signal.

Figure 2:
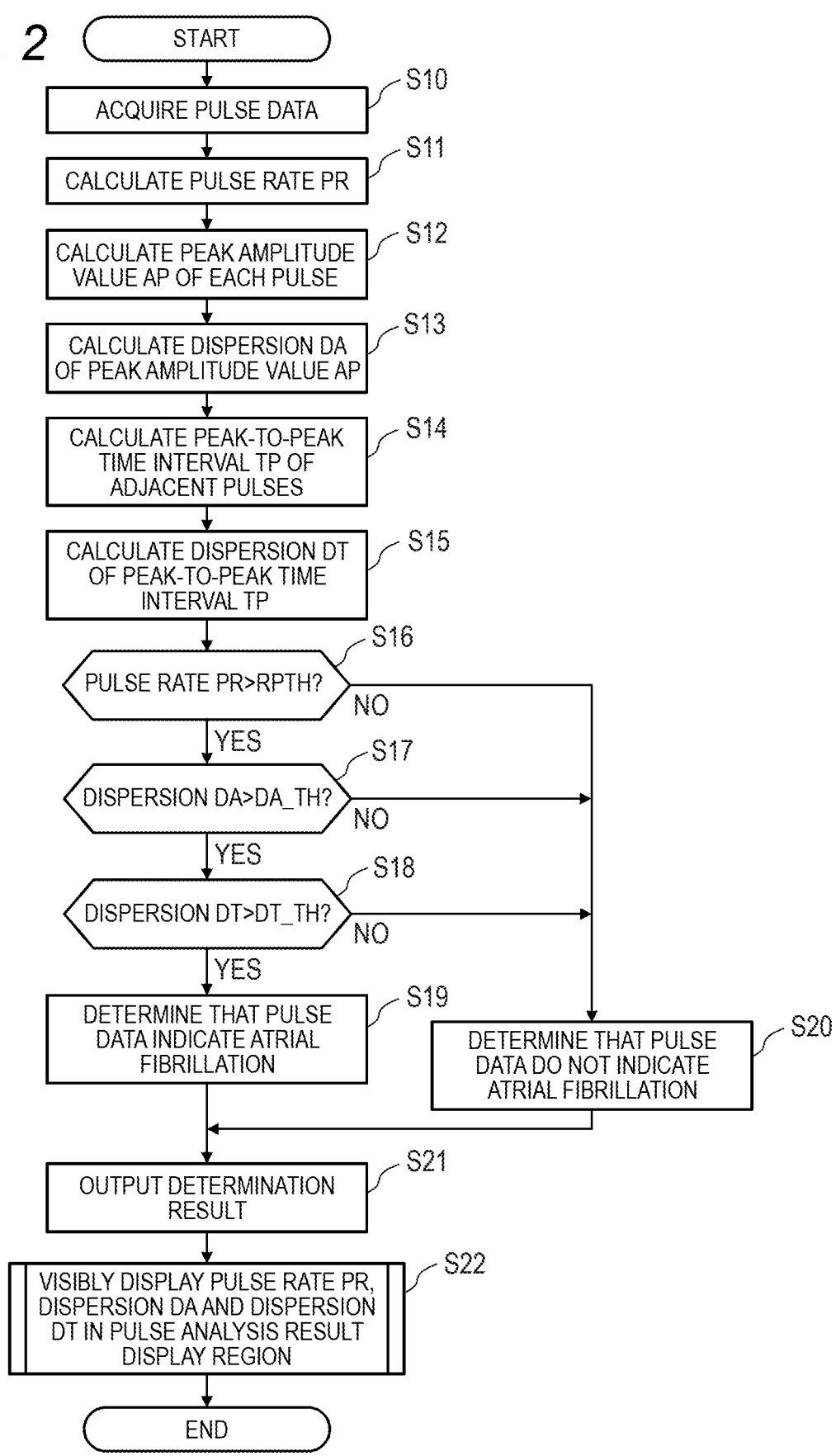
FIG. 2 is a flow chart for explaining an example of an atrial fibrillation detecting method according to the presently disclosed subject matter.
Figure 3:
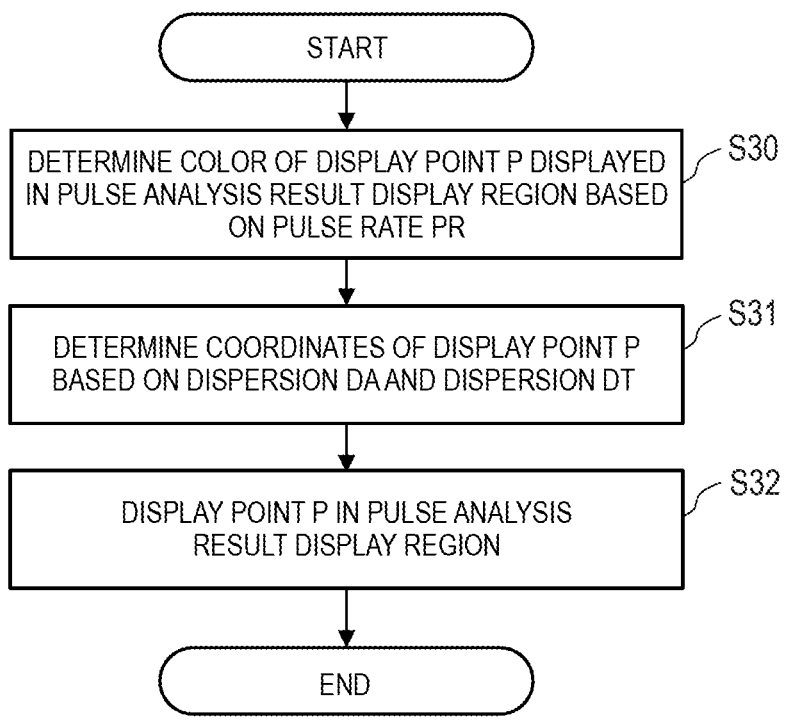
FIG. 3 is a flow chart for explaining an example of a method for visibly displaying a pulse rate, a dispersion of peak amplitude values and a dispersion of peak-to-peak time intervals on a pulse analysis result display region.

Next, an example of the atrial fibrillation detecting method according to the presently disclosed subject matter will be described with reference to FIGS. 2 to 4. FIG. 2 is a flow chart for explaining the example of the atrial fibrillation detecting method according to the presently disclosed subject matter. FIG. 3 is a flow chart for explaining an example of a method for visibly displaying a pulse rate, a dispersion Da of peak amplitude values Ap and a dispersion Dt of peak-to-peak time intervals Tp on a pulse analysis result display region R3 (see FIG. 4). FIG. 4 is a view illustrating an example of the physiological information display screen 10 which may include the pulse analysis result display region R3 displayed as a two-dimensional coordinate system.

As shown in FIG. 2, first, the controller 2 acquires pulse data of a patient (step S10). For example, the controller 2 may acquire the pulse data of the patient from the storage 3, or may acquire the pulse data through the network interface 4 from an external device disposed on the communication network. The controller 2 may acquire ECG data of the patient together with the pulse data of the patient in the step S10.

Next, the controller 2 calculates a pulse rate of the patient based on the acquired pulse data (step S11). Here, the pulse rate is a number of arterial pulses in one minute. In other words, the pulse rate corresponds to a number of pulses appearing in one minute. The controller 2 may calculate the pulse rate from the pulse data by use of a well-known analysis method. For example, after having acquired each of peak-to-peak time intervals Tp (an example of a pulse interval index) between adjacent ones of the pulses, the controller 2 calculates an average peak-to-peak time interval Tav of the peak-to-peak time intervals Tp. As illustrated in FIG. 4, each of the peak-to-peak time intervals Tp corresponds to a time interval between one peak point and the other point of two adjacent pulses. Then, the controller 2 may calculate a value (60 [sec]/Tav [sec]) which is obtained by dividing 60 seconds by the average peak-to-peak time interval Tav, as the pulse rate.

Next, the controller 2 calculates each of peak amplitude values Ap (an example of a pulse amplitude index) of a plurality (or all) of pulses contained in the pulse data based on the acquired pulse data (step S12). As shown in FIG. 4, each of the peak amplitude values Ap corresponds to an amplitude value of a pulse at a peak point thereof. Then, the controller 2 calculates a dispersion Da of the peak amplitude values Ap based on the calculated peak amplitude values Ap (step S13). For example, first, the controller 2 calculates a standard deviation $\sigma$ of the peak amplitude values Ap, and calculates an average value Ap_av of the peak amplitude values Ap. Next, the controller 2 divides the calculated standard deviation $\sigma$ of the peak amplitude values Ap by the average value Ap_av of the peak amplitude values Ap (standard deviation $\sigma$/average value Ap_av), so that a dispersion Da of the peak amplitude values Ap can be calculated. When the standard deviation $\sigma$ is divided thus by the average value Ap_av, the dispersion Da (Da<1) can be normalized.

In a step S14, the controller 2 calculates each of a plurality (or all) of peak-to-peak time intervals Tp (an example of a pulse interval index) contained in the pulse data. Incidentally, when the pulse rate is specified based on the peak-to-peak time intervals Tp in the step S11, the processing of the step S14 may be executed in the step S10. Then, the controller 2 calculates a dispersion Dt of the peak-to-peak time intervals Tp based on the calculated peak-to-peak time intervals Tp (step S15). For example, first, the controller 2 calculates a standard deviation σ of the peak-to-peak time intervals Tp, and calculates an average value Tp_av of the peak-to-peak time intervals Tp. Next, the controller 2 divides the calculated standard deviation σ of the peak-to-peak time intervals Tp by the average value Tp_av of the peak-to-peak time intervals Tp (standard deviation σ/average value Tp_av), so that a dispersion Dt of the peak-to-peak time intervals Tp can be calculated. When the standard deviation σ is divided thus by the average value Tp_av, the dispersion Dt (Dt<1) can be normalized.

Then, in a step S16, the controller 2 determines whether the specified pulse rate exceeds a threshold PRth (first threshold) or not. The threshold PRth may be changed suitably in accordance with an input operation performed by the medical care provider on the input operation unit 6. For example, the threshold PRth is 100 (times/minute). When it is determined that the calculated pulse rate exceeds the threshold PRth (YES in the step S16), the processing goes to a step S17. On the other hand, when it is determined that the calculated pulse rate does not exceed the threshold PRth (NO in the step S16), the processing goes to a step S20. In the step S20, the controller 2 determines that the pulse data of the patient do not indicate atrial fibrillation. In this case, the controller 2 may determine that the pulse data of the patient indicate regular pulses (normal sinus rhythm) or premature ventricular contraction.

Next, the controller 2 determines whether the calculated dispersion Da of the peak amplitude values Ap exceeds a threshold Da_th (second threshold) or not (step S17). The threshold Da_th may be changed suitably in accordance with an input operation performed by the medical care provider on the input operation unit 6. For example, Da_th is 0.2. When it is determined that the calculated dispersion Da exceeds the threshold Da_th (YES in the step S17), the processing goes to a step S18. On the other hand, when it is determined that the calculated dispersion Da does not exceed the threshold Da_th (NO in the step S17), the processing goes to the step S20.

Next, the controller 2 determines whether the calculated dispersion Dt of the peak-to-peak time intervals Tp exceeds a threshold Dt_th (third threshold) or not (the step S18). The threshold Dt_th may be changed suitably in accordance with an input operation performed by the medical care provider on the input operation unit 6. For example, Dt_th is 0.2. When it is determined that the calculated dispersion Dt exceeds the threshold Dt_th (YES in the step S18), the processing goes to a step S19. In the step S19, the controller 2 determines that the pulse data of the patient indicate atrial fibrillation. On the other hand, when it is determined that the calculated dispersion Dt does not exceed the threshold Dt_th (NO in the step S19), the processing goes to the step S20.

Then, in a step S21, the controller 2 outputs a determination result. For example, when it is determined that the pulse data indicate atrial fibrillation, the controller 2 may display, on the physiological information display screen 10 illustrated in FIG. 4, a message that the atrial fibrillation is suspected. On the other hand, when it is determined that the pulse data do not indicate atrial fibrillation, the controller 2 may display, on the physiological information display screen, a message that the atrial fibrillation is not suspected. Particularly, the determination result may be displayed in the pulse analysis result display region R3 in the physiological information display screen 10 which will be described later.

According to the presently disclosed subject matter, it is possible to provide a detecting device 1 which can determine whether the pulse data indicate atrial fibrillation or not, based on the pulse rate in addition to the dispersion Da of the peak amplitude values Ap and the dispersion Dt of the peak-to-peak time intervals Tp so that the atrial fibrillation can be detected more accurately. In this respect, according to the background art, it is possible to determine whether the pulse data indicate an arrhythmia or not, but it is not possible to accurately determine whether the pulse data indicate premature ventricular contraction or indicate atrial fibrillation. According to the presently disclosed subject matter, due to the parameter of the pulse rate which is newly added, it is possible to accurately determine that the pulse data indicate atrial fibrillation.

In addition, according to the presently disclosed subject matter, when it is determined that the pulse rate exceeds the threshold PRth, the dispersion Da of the peak amplitude values Ap exceeds the threshold Da_th and the dispersion Dt of the peak-to-peak time intervals Tp exceeds the threshold Dt_th (i.e. when all the processings in the steps S16 to S18 are YES), it is determined that the pulse data indicate atrial fibrillation. Threshold determination can be performed thus on the three parameters individually. Accordingly, the atrial fibrillation can be detected more accurately.

Return to FIG. 2. In a step S22, the controller 2 visibly displays the calculated pulse rate, and the dispersions Da and Dt in the pulse analysis result display region R3 (see FIG. 4). An example of the processing of the step S22 will be described below with reference to FIGS. 3 to 6.

First, as shown in FIG. 4, the physiological information display screen 10 displayed on the display 5 can include the ECG waveform display region R1 in which the ECG waveform drawn based on the ECG data is displayed, the pulse display region R2 in which the plurality of pulses rendered based on the pulse data are displayed, and the pulse analysis result display region R3 which is configured as the two-dimensional coordinate system including the vertical axis for the dispersion Da and the horizontal axis for the dispersion Dt.

Next, as shown in FIG. 3, first, the controller 2 calculates a color of a display point P displayed in the pulse analysis result display region R3 based on a calculated pulse rate (step S30). For example, when the pulse rate is lower than 70 (times/minute) (pulse rate<70), the controller 2 sets the color of the display point P at a first color (e.g. blue). When the pulse rate is not lower than 70 (times/minute) and not higher than 100 (times/minute) (70≤pulse rate≤100), the controller 2 sets the color of the display point P at a second color (e.g. yellow). When the pulse rate is higher than 100 (times/minute) (pulse rate>100), the controller 2 sets the color of the display point P at a third color (e.g. red).

In an example shown in FIG. 4, the pulse rate is 105. Accordingly, the controller 2 sets the color of the display point P at the third color. In addition, in an example of FIG. 5, the pulse rate is 63. Accordingly, the controller 2 sets the color of the display point P at the first color. Further, in an example of FIG. 6, the pulse rate is 73. Accordingly, the controller 2 sets the color of the display point P at the second color.

Next, the controller 2 determines coordinates of the display point P in the pulse analysis result display region R3 based on the calculated dispersions Da and Dt (step S31). For example, in an example illustrated in FIG. 4, Da=0.3 and Dt=0.21. Accordingly, the controller 2 sets the coordinates of the display point P at (0.21, 0.3). In an example illustrated in FIG. 5, Da=0.01 and Dt=0.02. Accordingly, the controller 2 sets the coordinates of the display point P at (0.02, 0.01). Further, in an example illustrated in FIG. 6, Da=0.19 and Dt=0.11. Accordingly, the controller 2 sets the coordinates of the display point P at (0.11, 0.19). Then, the controller 2 displays the display point P in the pulse analysis result display region R3 (step S32).

According to the presently disclosed subject matter, the dispersion Da of the peak amplitude values Ap and the dispersion Dt of the peak-to-peak time intervals Tp are visibly displayed (visualized) as one point on the two-dimensional coordinate system. Further, the color of the display point P displayed on the two-dimensional coordinate system is determined based on the pulse rate. Thus, the medical care provider can intuitively confirm whether the determination result executed by the detecting device 1 is correct or not.

Incidentally, the pulse analysis result display region R3 may be visibly displayed as a three-dimensional coordinate system. In this case, the pulse analysis result display region R3 is configured as a three-dimensional coordinate system (three-dimensional coordinate space) including a first axis for the pulse rate, a second axis for the dispersion Da, and a third axis for the dispersion Dt. Further, the controller 2 visibly displays the calculated pulse rate and the calculated dispersions Da and Dt as one point on the three-dimensional coordinate system (pulse analysis result display region R3). Particularly, the controller 2 determines coordinates of the display point P to be displayed in the pulse analysis result display region R3 based on the calculated pulse rate and the calculated dispersions Da and Dt. Thus, the calculated pulse rate and the calculated dispersions Da and Dt are visibly displayed as one point on the three-dimensional coordinate system. Accordingly, the medical care provider can more accurately confirm whether the determination result executed by the detecting device 1 is correct or not. When the pulse analysis result display region R3 is configured as the three-dimensional coordinate system, the pulse analysis result display region R3 may be displayed in the physiological information display screen 10 or may be displayed in a window screen provided separately from the physiological information display screen 10.

In addition, in order to implement the detecting device 1 according to the presently disclosed subject matter by software, the atrial fibrillation detecting program may be incorporated into the storage 3 or the ROM in advance. In addition, the atrial fibrillation detecting program may be stored into a computer-readable storage medium such as a magnetic disk (such as an HDD or a floppy disk), an optical disk (such as a CD-ROM, a DVD-ROM or a Blu-ray disk), a magneto-optical disk (such as an MO), or a flash memory (such as an SD card, a USB memory or an SSD). In this case, the atrial fibrillation detecting program stored in the storage medium is read by a disk drive etc. provided in the detecting device 1. Thus, the atrial fibrillation detecting program is incorporated into the storage 3. The program incorporated into the storage 3 is loaded onto the RAM, and the processor executes the program loaded onto the RAM. Thus, the atrial fibrillation detecting method illustrated in FIG. 2 can be executed.

In addition, the atrial fibrillation detecting program may be downloaded from a computer on the communication network through the network interface 4. Also in this case, the downloaded program is incorporated into the storage 3 in a similar manner or the same manner.

Although the presently disclosed subject matter has been described above, the technical scope of the present disclosure should not be interpreted limitedly to the description of the presently disclosed subject matter. The presently disclosed subject matter is merely exemplified. It should be understood by those skilled in the art that various changes may be made on the presently disclosed subject matter within the scope of the present disclosure stated in Claims. The technical scope of the present disclosure should be defined based on the scope of the present disclosure stated in the Claims and an equivalent scope thereto.

In addition, in the presently disclosed subject matter, the peak amplitude value Ap and the peak-to-peak time interval Tp have been described as the example of the pulse amplitude index and the example of the pulse interval index respectively. However, the pulse interval index and the pulse amplitude index should not be limited to the peak-to-peak time interval Tp and the peak amplitude value Ap respectively.

For example, in the presently disclosed subject matter, the following indices may be used as the pulse interval index.

A time interval between a time point when a pulse rises and a time point when an incisure of the pulse is generated A time interval between a time point when an incisure of a pulse is generated and a time point when a next pulse rises A time interval between a time point when a pulse rises and a time point when a next pulse rises For example, in the presently disclosed subject matter, the following indices may be used as examples of the pulse amplitude index.

An area of a pulse between a time point when the pulse rises and a time point when a next pulse rises An area of a pulse between a time point when the pulse rises and a time point when an incisure of the pulse is generated

What is claimed is:

1. An atrial fibrillation detecting device comprising:
a pulse sensor;
a processor;
a display; and
a memory that stores a computer-readable command,
wherein, when the computer-readable command is executed by the processor, the atrial fibrillation detecting device is configured to:
acquire, from the pulse sensor, pulse data representing a plurality of pulses;
calculate a pulse rate based on the pulse data;
calculate respective pulse amplitude indices of the plurality of pluses based on the pulse data;
calculate an amplitude dispersion of the pulse amplitude indices based on the calculated pulse amplitude indices;
calculate respective pulse interval indices of the plurality of pluses based on the pulse data;
calculate an interval dispersion of the pulse interval indices based on the calculated pulse interval indices; and
determine whether the pulse data is atrial fibrillation, based on the calculated pulse rate, the calculated amplitude dispersion, and the calculated interval dispersion; and
display on the display an indication of whether the pulse data is an atrial fibrillation based on the determination.

2. The atrial fibrillation detecting device according to claim 1, wherein, when the computer-readable command is executed by the processor, the atrial fibrillation detecting device is configured to:
determine whether the calculated pulse rate exceeds a first threshold or not;

determine whether the calculated amplitude dispersion exceeds a second threshold or not;
determine whether the calculated interval dispersion exceeds a third threshold or not; and
determine that the pulse data is atrial fibrillation when it is determined that the calculated pulse rate exceeds the first threshold, the calculated amplitude dispersion exceeds the second threshold and the calculated interval dispersion exceeds the third threshold.

3. The atrial fibrillation detecting device according to claim 1, wherein, when the computer-readable command is executed by the processor, the atrial fibrillation detecting device is configured to:
calculate the amplitude dispersion by calculating a standard deviation of the pulse amplitude indices, calculating an average value of the pulse amplitude indices, and dividing the calculated standard deviation by the calculated average value; and
calculate the interval dispersion by calculating a standard deviation of the pulse interval indices, calculating an average value of the pulse interval indices, and dividing the calculated standard deviation by the calculated average value.

4. The atrial fibrillation detecting device according to claim 1, wherein, when the computer-readable command is executed by the processor, the atrial fibrillation detecting device visibly displays, on the display, the calculated pulse rate, the calculated amplitude dispersion and the calculated interval dispersion on a two-dimensional coordinate system or a three-dimensional coordinate system.

5. The atrial fibrillation detecting device according to claim 4, wherein, when the computer-readable command is executed by the processor, the atrial fibrillation detecting device is configured to:
visibly display on the display the calculated dispersion of the pulse amplitude indices and the calculated dispersion of the pulse interval indices as one point on a two-dimensional coordinate system;
determine a color of the point displayed on the two-dimensional coordinate system based on the specified pulse rate; and
determine coordinates of the point displayed on the two-dimensional coordinate system based on the calculated dispersion of the pulse amplitude indices and the calculated dispersion of the pulse interval indices.

6. The atrial fibrillation detecting device according to claim 4, wherein, when the computer-readable command is executed by the processor, the atrial fibrillation detecting device is configured to:
visibly display on the display the calculated pulse rate, the calculated amplitude dispersion and the calculated interval dispersion as one point on a three-dimensional coordinate system; and
calculate coordinates of the point displayed on the three-dimensional coordinate system based on the calculated pulse rate, the calculated amplitude dispersion and the calculated interval dispersion.

7. The atrial fibrillation detecting device according to claim 1, wherein each of the pulse amplitude indices is a peak amplitude value, and each of the pulse interval indices is a peak-to-peak time interval between adjacent pulses.

8. An atrial fibrillation detecting method that is executed, the method comprising:
acquiring, from a pulse sensor, pulse data representing a plurality of pulses;
calculating a pulse rate based on the pulse data;
calculating respective pulse amplitude indices of the plurality of pluses based on the pulse data;
calculating an amplitude dispersion of the pulse amplitude indices based on the calculated pulse amplitude indices;
calculating respective pulse interval indices of the plurality of pluses based on the pulse data;
calculating an interval dispersion of the pulse interval indices based on the calculated pulse interval indices; and
determining whether the pulse data is atrial fibrillation, based on the calculated pulse rate, the calculated amplitude dispersion, and the calculated interval dispersion; and
displaying on a display an indication of whether the pulse data is an atrial fibrillation based on the determination.

9. The atrial fibrillation detecting method according to claim 8, wherein the determining includes:
determining whether the calculated pulse rate exceeds a first threshold or not;
determining whether the calculated amplitude dispersion exceeds a second threshold or not;
determining whether the calculated interval dispersion exceeds a third threshold or not; and
determining that the pulse data is atrial fibrillation when it is determined that the calculated pulse rate exceeds the first threshold, the calculated amplitude dispersion exceeds the second threshold and the calculated interval dispersion exceeds the third threshold.

10. The atrial fibrillation detecting method according to claim 8 further comprising:
visibly displaying, on the display, the calculated pulse rate, the calculated amplitude dispersion and the calculated interval dispersion on a two-dimensional coordinate system or a three-dimensional coordinate system.

11. The atrial fibrillation detecting method according to claim 10, wherein, the calculated amplitude dispersion and the calculated interval dispersion are visibly displayed as one point on a two-dimensional coordinate system, and the displaying includes:
determining a color of the point displayed on the two-dimensional coordinate system based on the calculated pulse rate, and
determining coordinates of the point displayed on the two-dimensional coordinate system based on the calculated dispersion of the pulse amplitude indices and the calculated dispersion of the pulse interval indices.

12. The atrial fibrillation detecting method according to claim 10, wherein, the calculated pulse rate, the calculated dispersion of the pulse amplitude indices and the calculated dispersion of the pulse interval indices are visibly displayed as one point on a three-dimensional coordinate system; and
the displaying includes calculating coordinates of the point displayed on the three-dimensional coordinate system based on the calculated pulse rate, the calculated amplitude dispersion and the calculated interval dispersion.

13. The atrial fibrillation detecting method according to claim 8, wherein each of the pulse amplitude indices is a peak amplitude value; and each of the pulse interval indices is a peak-to-peak time interval between adjacent pulses.

14. A computer-readable storage medium storing a program causing a computer to execute the atrial fibrillation detecting method according to claim 8.

* * * * *